US009387105B2

(12) United States Patent
 Andress et al.

(10) Patent No.: US 9,387,105 B2
(45) Date of Patent: Jul. 12, 2016

(54) SLEEVES FOR EXPANDABLE MEDICAL DEVICES AND METHODS OF MAKING THE SAME

(71) Applicant: W. L. Gore & Associates, Inc., Newark, DE (US)

(72) Inventors: Murray F. B. Andress, Flagstaff, AZ (US); Patrick M. Norris, Bellemont, AZ (US)

(73) Assignee: W.L. GORE & ASSOCIATES, INC, Newark, DE (US)

( * ) Notice: Subject to any disclaimer, the term of this patent is extended or adjusted under 35 U.S.C. 154(b) by 122 days.

(21) Appl. No.: 14/076,788

(22) Filed: Nov. 11, 2013

(65) Prior Publication Data

US 2014/0135895 A1    May 15, 2014

Related U.S. Application Data

(60) Provisional application No. 61/725,389, filed on Nov. 12, 2012.

(51) Int. Cl.
*A61F 2/06*    (2013.01)
*A61F 2/962*    (2013.01)
*A61F 2/97*    (2013.01)

(52) U.S. Cl.
CPC .. *A61F 2/962* (2013.01); *A61F 2/97* (2013.01)

(58) Field of Classification Search
CPC ............. A61F 2/95; A61F 2/962; A61F 2/97; A61F 2002/9583; A61F 2002/9665; A61F 2/954; A61F 2/966
See application file for complete search history.

(56) References Cited

U.S. PATENT DOCUMENTS

| 6,514,281 | B1 | 2/2003 | Blaeser et al. | |
|---|---|---|---|---|
| 8,066,756 | B2 | 11/2011 | Rasmussen et al. | |
| 8,252,015 | B2 | 8/2012 | Leeflang et al. | |
| 2006/0085057 | A1 | 4/2006 | George et al. | |
| 2011/0230951 | A1* | 9/2011 | Cully et al. | 623/1.11 |
| 2012/0130475 | A1 | 5/2012 | Shaw | |
| 2013/0297007 | A1* | 11/2013 | Kuchela | A61M 25/0662 623/1.23 |

FOREIGN PATENT DOCUMENTS

WO    2013/137977    9/2013

OTHER PUBLICATIONS

International Search Report for PCT/US2013/069660 mailed Feb. 10, 2014, corresponding to U.S. Appl. No. 14/076,788.

* cited by examiner

*Primary Examiner* — Melanie Tyson

(57) ABSTRACT

Various aspects describe treatment of the vasculature of a patient with an expandable implant. The implant is surrounded and constrained by one or more constraining sleeves. One or more of these sleeves may include an end profile with a desired shape, and constrain the expandable implant in a configuration having a diameter less than the diameter of an unconstrained diameter of the expandable implant.

10 Claims, 6 Drawing Sheets

SLEEVES FOR EXPANDABLE MEDICAL DEVICES AND METHODS OF MAKING THE SAME

BACKGROUND

1. Field

The present disclosure relates to the transcatheter delivery and remote deployment of implantable medical devices and, more particularly, implantable expandable devices surrounded by constraining sleeves.

2. Discussion of the Related Art

Endoluminal therapies typically involve the insertion of a delivery catheter that transports an implantable prosthetic device into the vasculature through a small, often percutaneous, access site in a remote vessel. Once access to the vasculature is achieved, the delivery catheter is used to mediate intraluminal delivery and subsequent deployment of the prosthesis via one of several techniques. In this fashion, the prosthesis can be remotely implanted to achieve a therapeutic outcome. In contrast to conventional surgical therapies, endoluminal treatments are distinguished by their "minimally invasive" nature.

Expandable endoprostheses are generally comprised of a stent component with or without a graft covering over the stent interstices. They are designed to spontaneously dilate (i.e., elastically recover) or to be balloon-expanded from their delivery diameter, through a range of intermediary diameters, up to a maximal, pre-determined functional diameter. The endoluminal delivery and deployment of expandable endoprostheses pose several unique problems. First, the endoprosthesis itself must be radially compacted to a suitable introductory size (or delivery diameter) to allow insertion into the vasculature, then it must be constrained in that compacted state and mounted onto a delivery device such as a catheter shaft. Subsequently, the constraint must be removed in order to allow the endoprosthesis to expand to its functional diameter and achieve the desired therapeutic outcome. A variety of ways of constraining and releasing an expandable device are known in the art. For example, an expandable device may be constrained by one or more constraining sleeves.

It remains desirable to provide improved systems for endoluminal delivery of stents or stent grafts to vascular treatment sites. Therefore, devices, systems and methods that facilitate improved preparation of a sleeve-constrained expandable implant for delivery, accurate delivery of the implant, and correct orientation and position of the implant would be useful and desirable.

BRIEF DESCRIPTION OF THE DRAWINGS

The accompanying drawings are included to provide a further understanding of the disclosure and are incorporated in and constitute a part of this specification, illustrate embodiments of the disclosure, and together with the description serve to explain the principles of the disclosure, wherein.

DETAILED DESCRIPTION OF THE ILLUSTRATED EMBODIMENTS

Figure 1A:
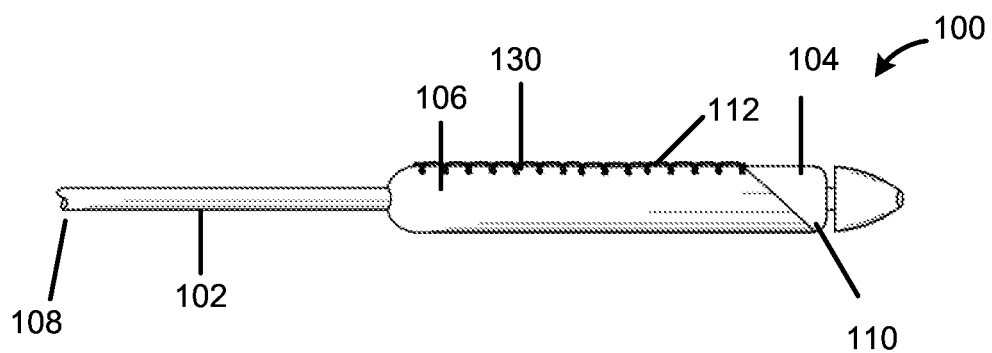
FIGS. 1A and 1B are side and perspective views of a system for implanting a medical device within a patient.

Persons skilled in the art will readily appreciate that various aspects of the present disclosure can be realized by any number of methods and apparatuses configured to perform the intended functions. Stated differently, other methods and apparatuses can be incorporated herein to perform the intended functions. It should also be noted that the accompanying drawing figures referred to herein are not all drawn to scale, but can be exaggerated to illustrate various aspects of the present disclosure, and in that regard, the drawing figures should not be construed as limiting.

Throughout this specification and in the claims, the term "distal" refers to a location, or a portion of an expandable implant (such as a stent-graft), that is further downstream with respect to blood flow than another portion of the device. Similarly, the term "distally" refers to the direction of blood flow or further downstream in the direction of blood flow.

The term "proximal" refers to a location, or a portion of an expandable implant, that is, further upstream with respect to blood flow than another portion of the device. Similarly, the term "proximally" refers to the direction opposite to the direction of blood flow or upstream from the direction of blood flow.

Various embodiments of the present disclosure comprise a catheter assembly configured to deliver an expandable implant to a treatment area of the vasculature of a patient. In accordance with embodiments of the disclosure, an expandable implant, such as a stent graft, is constrained by one or more sleeves concentrically surrounding the expandable implant. One or more of these sleeves comprises an end profile having a desired shape. The end profile may assist in deploying the expandable device by, among other things, facilitating withdrawal of the sleeve from the implant and assisting in bending, curving, and/or conforming the expandable implant within the vasculature of the patient.

Figure 1B:
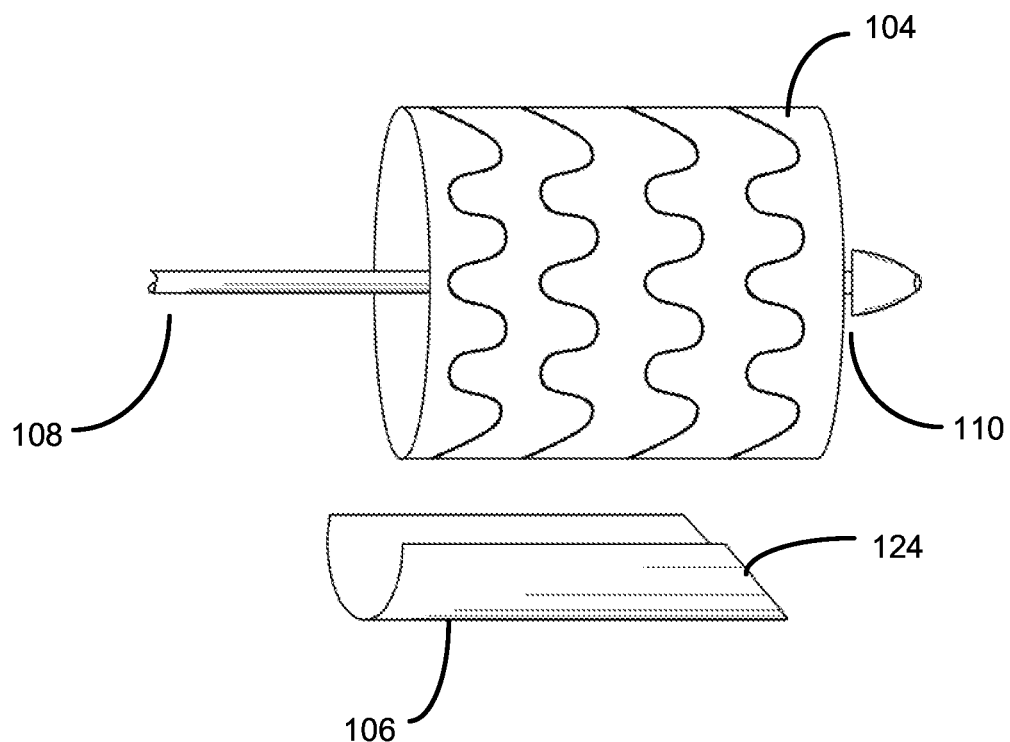

With reference to FIGS. 1A and 1B, a catheter assembly 100 in accordance with the present disclosure is illustrated. Catheter assembly 100 comprises a catheter shaft 102 having a distal end 108 and a proximal end 110. Located near proximal end 110 is an expandable implant 104. Expandable implant 104 is concentrically surrounded by at least one constraining sleeve, such as first sleeve 106.

In various embodiments, expandable implant 104 comprises a stent graft. Conventional stent grafts are designed to dilate from their delivery diameter, through a range of intermediary diameters, up to a maximum, often pre-determined functional diameter, and generally comprise one or more stent components with one or more graft members displaced over and/or under the stent.

In various embodiments, expandable implant 104 comprises one or more stent components made of nitinol and a graft member made of ePTFE. However, and as discussed below, any suitable combination of stent component(s) and graft member(s) is within the scope of the present disclosure.

For example, stent components can have various configurations such as, for example, rings, cut tubes, wound wires (or ribbons) or flat patterned sheets rolled into a tubular form. Stent components can be formed from metallic, polymeric or natural materials and can comprise conventional medical grade materials such as nylon, polyacrylamide, polycarbonate, polyethylene, polyformaldehyde, polymethylmethacrylate, polypropylene, polytetrafluoroethylene, polytrifluorochlorethylene, polyvinylchloride, polyurethane, elastomeric organosilicon polymers; metals such as stainless steels, cobalt-chromium alloys and nitinol and biologically derived materials such as bovine arteries/veins, pericardium and collagen. Stent components can also comprise bioresorbable materials such as poly(amino acids), poly(anhydrides), poly (caprolactones), poly(lactic/glycolic acid) polymers, poly (hydroxybutyrates) and poly(orthoesters). Any expandable stent component configuration which can be delivered by a catheter is in accordance with the present disclosure.

Moreover, potential materials for graft members include, for example, expanded polytetrafluoroethylene (ePTFE), polyester, polyurethane, fluoropolymers, such as perfouorelastomers and the like, polytetrafluoroethylene, silicones, urethanes, ultra high molecular weight polyethylene, aramid fibers, and combinations thereof. Other embodiments for a graft member material can include high strength polymer fibers such as ultra high molecular weight polyethylene fibers (e.g., Spectra®, Dyneema Purity®, etc.) or aramid fibers (e.g., Technora®, etc.). The graft member can include a bioactive agent. In one embodiment, an ePTFE graft includes a carbon component along a blood contacting surface thereof. Any graft member which can be delivered by a catheter is in accordance with the present disclosure.

In various embodiments, a stent component and/or graft member can comprise a therapeutic coating. In these embodiments, the interior or exterior of the stent component and/or graft member can be coated with, for example, a CD34 antigen. Additionally, any number of drugs or therapeutic agents can be used to coat the graft member, including, for example heparin, sirolimus, paclitaxel, everolimus, ABT-578, mycophenolic acid, tacrolimus, estradiol, oxygen free radical scavenger, biolimus A9, anti-CD34 antibodies, PDGF receptor blockers, MMP-1 receptor blockers, VEGF, G-CSF, HMG-CoA reductase inhibitors, stimulators of iNOS and eNOS, ACE inhibitors, ARBs, doxycycline, and thalidomide, among others.

In various embodiments, expandable implant 104 can comprise a radially collapsed configuration suitable for delivery to the treatment area of the vasculature of a patient. Expandable implant 104 can be constrained in a radially collapsed configuration and mounted onto a delivery device such as catheter shaft 102. The diameter of the expandable implant 104 in the collapsed configuration is small enough for the implant to be delivered through the vasculature to the treatment area. In various embodiments, the diameter of the collapsed configuration is small enough to minimize the crossing profile of catheter assembly 100 and reduce or prevent tissue damage to the patient. In the collapsed configuration, the expandable implant 104 can be guided by catheter shaft 102 through the vasculature. Once in position in the treatment area of the vasculature, expandable implant 104 can be expanded to a radially expanded configuration.

In various embodiments, expandable implant 104 can comprise a radially expanded configuration suitable for implanting the device in the treatment area of a patient's vasculature. In the expanded configuration, the diameter of expandable implant 104 can be approximately the same as the vessel to be repaired. In other embodiments, the diameter of expandable implant 104 in the expanded configuration can be slightly larger than the vessel to be treated to provide a traction fit within the vessel.

In various embodiments, expandable implant 104 can comprise a self-expandable device, such as a self-expandable stent graft. Such devices dilate from a radially collapsed configuration to a radially expanded configuration when unrestrained. In other embodiments, expandable implant 104 can comprise a device that is expanded with the assistance of a secondary device such as, for example, a balloon. In yet other embodiments, catheter assembly 100 can comprise a plurality of expandable implants 104. The use of a catheter assembly with any number of expandable implants is within the scope of the present disclosure.

Various medical devices in accordance with the disclosure comprise a sleeve or multiple sleeves. The sleeve or sleeves can constrain an expandable implant device in a collapsed configuration for endoluminal delivery of the implant to a treatment portion of the vasculature of a patient. For the purposes of the disclosure, the term "constrain" can mean (i) to limit the expansion, either through self-expansion or assisted by a device, of the diameter of an expandable implant or (ii) to cover or surround but not otherwise restrain an expandable implant (e.g., for storage or biocompatibility reasons and/or to provide protection to the expandable implant and/or the vasculature). For example, as illustrated in FIGS. 1A and 1B, catheter assembly 100 comprises first sleeve 106. First sleeve 106 surrounds and constrains expandable implant 104 to a reduced diameter.

After delivery of the expandable implant to the treatment portion of the vasculature of the patient, the sleeve or sleeves can be unconstrained in order to allow the expandable implant to expand to its functional diameter and achieve the desired therapeutic outcome. In various embodiments, the sleeve or sleeves can remain implanted while not interfering with the expandable implant. In other embodiments, the sleeve or sleeves can be removed from the body of the patient after successful deployment of the expandable implant.

As will be discussed in greater detail below, in various embodiments, an expandable implant is constrained by a single sleeve which circumferentially surrounds the expandable implant. In other embodiments, an expandable implant is constrained by a plurality of sleeves which circumferentially surround the expandable implant. The plurality of sleeves can comprise at least two sleeves which circumferentially surround each other.

In various embodiments, the constraining sleeve or sleeves comprise two ends, and each end has an end profile that is different from the other end. For example, with reference to FIGS. 2A-2C, various sleeves 106 are illustrated. Sleeves 106 comprise a first end 214 and a second end 216. First end 214 has a first end profile 224. In various embodiments, first end 214 comprises a circular profile perpendicular to a central axis 230.

Figure 2A:
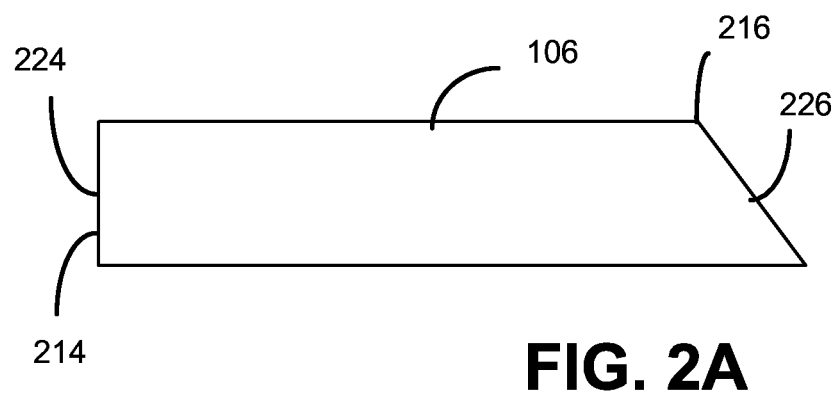
FIGS. 2A, 2B, and 2C are side views of various constraining sleeves.
Figure 2B:
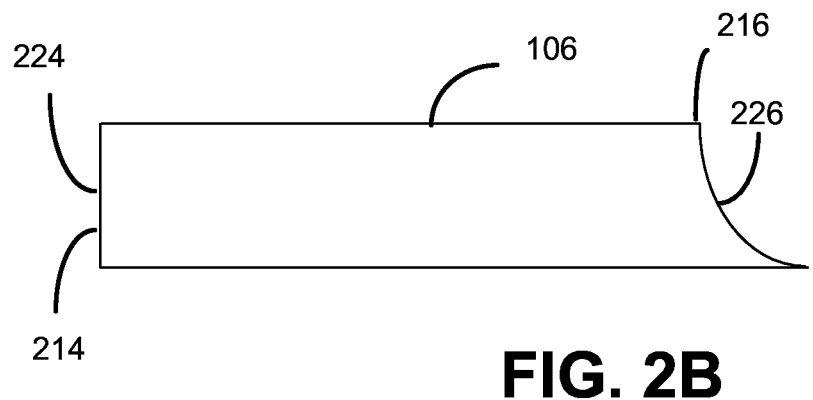
Figure 2C:
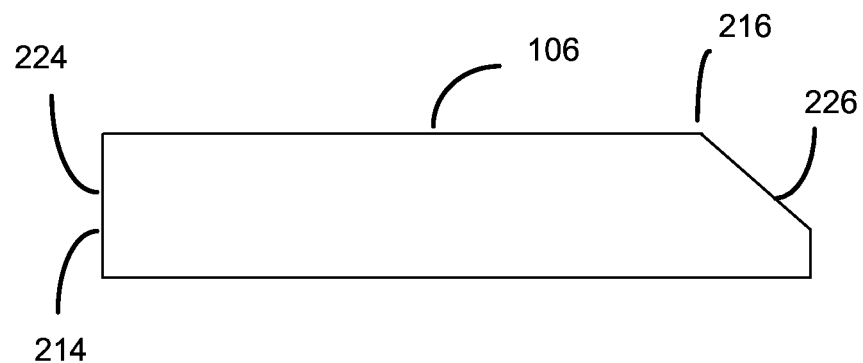

In various embodiments, second end 216 comprises a second end profile 226. As illustrated in FIGS. 2A-2C, second end profiles 226 comprise various shapes that are different from first end profile 224. In such configurations, second end profiles 226 comprise shapes that are different from a circular shape that is perpendicular to central axis 230. The perimeter of second end profiles 226 is greater than the perimeter of first end profiles 224. For example, FIG. 2A illustrates a sleeve 106 having a second end profile 226 that comprises a shape, the face of which is at a constant angle relative to central axis 230.

FIG. 2B illustrates a sleeve 106 having a second end profile 226 comprises a shape that has a face which is not at a constant angle relative to central axis 230. For example, second end profile 226 can comprise a curved shape. FIG. 2C illustrates a sleeve 106 having a second end profile 226 wherein only a portion of second end profile 226 comprises a shape that has a face which is at a constant angle relative to the central axis 230.

In other embodiments, first end profile 224 and second end profile 226 are non-perpendicular. In such configurations, a face corresponding to the shape of first end profile 224 is not perpendicular to a face corresponding to the shape of second end profile 226. Although illustrated in three specific examples, second end profiles 226 of sleeve 106 can comprise any shape other than a circular shape normal to central axis or any configuration in which the perimeter of second end profile 226 is greater than the perimeter of first end profile 224.

In various embodiments, second end profile 226 is formed by cutting or manipulating sleeve 106. For example, second end profile 226 can be formed by cutting second end 216 of sleeve 106 at a constant angle. In other embodiments, second end 216 can be formed by cutting sleeve 106 according to a predetermined pattern or shape. Any manner of forming second end profile 226 from second end 216 of sleeve 106 is within the scope of the present disclosure.

Second end profile 226 can assist in deployment of expandable implant 104. For example, second end profile 226 can expose a portion of expandable implant 104 (such as, in the case of a stent graft, one or more apices of the stent) to the vasculature of the patient. Further, second end profile 226 can assist, among other things, in the withdrawal or removal of one or more sleeves, such as sleeve 106, after expandable implant 104 has been expanded from the compressed configuration.

In various embodiments, sleeves such as sleeve 106 can be formed from a sheet of one or more materials wrapped or folded about the expandable implant. While the illustrative embodiments herein are described as comprising one or more tubular sleeves, sleeves of any non-tubular shape that corresponds to an underlying expandable implant or that are otherwise appropriately shaped for a given application are also within the scope of the present disclosure.

In various embodiments, sleeves are formed by wrapping or folding the sheet of material(s) such that two parallel edges of the sheet are substantially aligned. Said alignment can or can not be parallel to or coaxial with the catheter shaft of a catheter assembly. In various embodiments, the edges of the sheet of material(s) do not contact each other.

In various embodiments, the edges of the sheet of material(s) do contact each other and are coupled with a coupling member (as described below), an adhesive, or the like. In various other embodiments, the edges of the sheet of material(s) are aligned so that the edges of the same side of the sheet or sheets (e.g., the front/first major surface or back/second major surface of the sheet) are in contact with each other. In still other embodiments, the edges of opposite sides of the sheet of material(s) are in contact with each other, such that the edges overlap each other, such that a portion of one side of the sheet is in contact with a portion of the other side. Said another way, the front of the sheet can overlap the rear of the sheet, or vice versa.

In various embodiments, sleeves comprise materials similar to those used to form a graft member. For example, a precursor flexible sheet used to make the sleeve can be formed from a flattened, thin wall ePTFE tube. The thin wall tube can incorporate "rip-stops" in the form of longitudinal high strength fibers attached or embedded into the sheet or tube wall.

The sheet of material(s) used to form the sleeve(s) can comprise a series of openings, such that the openings extend from one edge of the sheet to the other. In such configurations, a coupling member can be woven or stitched through the series of openings in the sheet of material(s), securing each of the two edges together and forming a tube. For example, in FIG. 1, coupling member 112 engages with first plurality of holes 130 and secures the edges of sleeve 106 such that sleeve 106 maintains expandable implant 104 in a reduced diameter.

In various embodiments, a second end profile of a constraining sleeve is formed by creating a shape that corresponds to the desired second end profile in the sheet prior to forming the sleeve. For example, with reference to FIGS. 3A-3C, various sheets 340 used to form sleeves 106 are illustrated. In various embodiments, sheet 340 comprising a second end shape 342. Second end shape 342 can correspond to a desired second end profile 226 of sleeve 106.

Figure 3A:
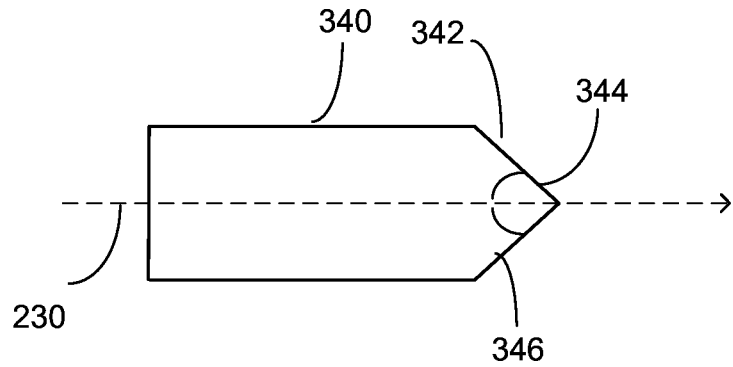
FIGS. 3A, 3B, and 3C are top views of sheets of material used to form constraining sleeves.

Second end shape 342 can comprise a first line 344 and a second line 346. For example, as illustrated in FIG. 3A, first line 344 and second line 346 comprise generally symmetrical, straight lines. First line 344 and second line 346 form generally the same angles in relation to central axis 230. In such configurations, second end shape 342 comprises a generally symmetrical triangle.

Figure 3B:
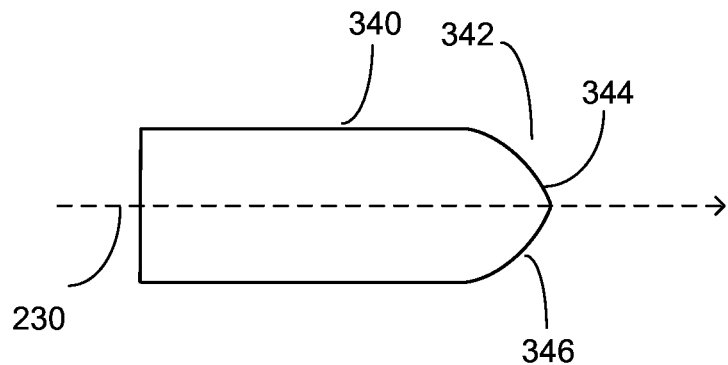

In other embodiments, as illustrated in FIG. 3B, first line 344 and second line 346 comprise generally symmetrical, non-straight lines. First line 344 and second line 346 can be either concave or convex.

Figure 3C:
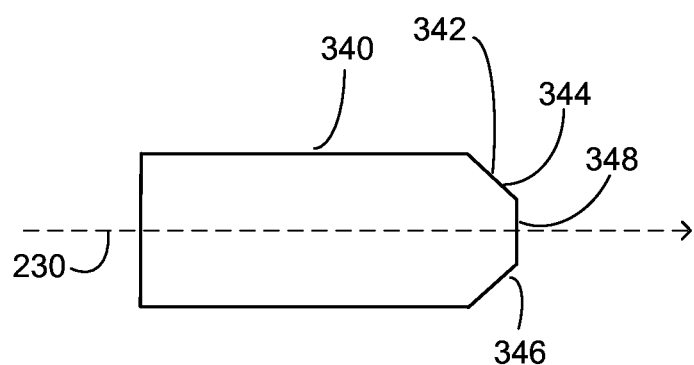

In yet other embodiments, as illustrated in FIG. 3C, second end shape 342 comprises a first line 344, second line 346, and third line 348. In such configurations, first line 344 and second line 346 can be symmetrical, and third line 348 can intersect first line 344 and second line 346 at the same point along both lines. In such configurations, second end shape 342 comprises a generally trapezoidal shape. Although described in regards to these specific examples, second end shape 342 can comprise any desired shape.

With reference to FIGS. 1A and 1B, catheter assembly 100 comprises a single first sleeve 106. As previously discussed, in various embodiments, first sleeve 106 circumferentially surrounds expandable implant 104 and constrains it in a collapsed configuration, in which the diameter is less than the diameter of the unconstrained implant. For example, sleeve 106 can constrain expandable implant 104 in a collapsed configuration for delivery within the vasculature.

In various embodiments, catheter assembly 100 further comprises a coupling member 112 that retains sleeve 106 in relation to expandable implant 104. In such configurations, sleeve 106 comprises a plurality of holes 130. Coupling member 112 engages with the plurality of holes 130 and maintains sleeve 106 in a generally tubular configuration surrounding expandable implant 104.

In various embodiments, when the expandable implant is in position within the vasculature, the coupling member or members can be disengaged from the sleeve or sleeves from outside of the body of the patient, which allows the sleeve(s) to open and the expandable implant to expand. As discussed above, the expandable implant can be self-expanding, or the implant can be expanded by a device, such as a balloon.

Coupling members can comprise a woven fiber. In other embodiments, the coupling member can comprise a monofilament fiber. Any type of string, cord, thread, fiber, or wire which is capable of maintaining a sleeve in a tubular shape is within the scope of the present disclosure.

The coupling member or members can be disengaged from the sleeve or sleeves by a mechanical mechanism operated from outside of the body of the patient. For example, the member or members can be disengaged by applying sufficient tension to the member or members. In another example, a dial or rotational element can be attached to the coupling member or members outside of the body. Rotation of the dial or rotational element can provide sufficient tension to, displace and disengage the coupling member or members.

In various embodiments, disengaging a single coupling member which closes a single sleeve from the sleeve allows the expandable device to be fully expanded. For example, with reference to FIG. 1A, catheter assembly 100 can be used to deliver an expandable implant 104 to a treatment area of a vasculature. In such configurations, first sleeve 106 circumferentially surrounds expandable implant 104 and constrains it to a collapsed configuration. Once expandable implant 104 is in position relative to the treatment area, coupling member 112 is disengaged from first sleeve 106 and first sleeve 106 is released, allowing expandable implant 104 to expand from a collapsed configuration to a larger diameter.

In other embodiments, catheter assembly 100 can comprise multiple sleeves. For example, with reference to FIGS. 4A-4D, expandable implant 104 is concentrically surrounded by a first sleeve 106 and a second sleeve 456. In such configurations, first sleeve 106 constrains expandable implant 104 in a collapsed configuration. By removing and/or activating first coupling member 112, first sleeve 106 can be removed and expandable implant 104 can expand to a configuration having a larger diameter than in the collapsed configuration.

For example, in various embodiments, second sleeve 456 constrains expandable implant 104 in an intermediate configuration. In the intermediate configuration, the diameter of expandable implant 104 is constrained in a diameter smaller than the expanded configuration and larger than the collapsed configuration. For example, the diameter of expandable device 104 in the intermediate configuration can be about 50% of the diameter of expandable device 104 in the expanded configuration. However, any diameter of the intermediate configuration which is less than the diameter of the expanded configuration and larger than the collapsed configuration is within the scope of the disclosure.

In such embodiments, expandable implant 104 can be expanded from the collapsed configuration to the intermediate configuration once expandable implant 104 has been delivered near the treatment area of the vasculature of a patient. The intermediate configuration can, among other things, assist in properly orienting and locating the expandable implant within the treatment area of the vasculature.

Figure 4A:
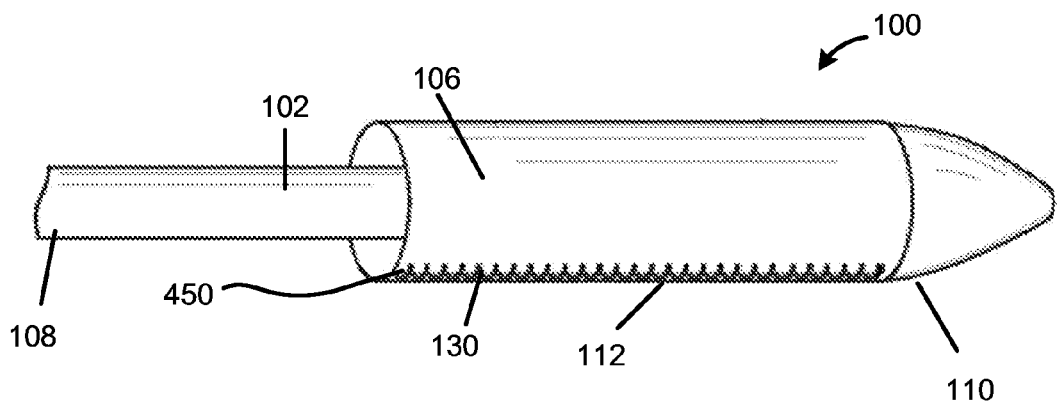
FIGS. 4A, 4B, 4C, and 4D are side and perspective views of a catheter assembly having an expandable medical device.
Figure 4B:
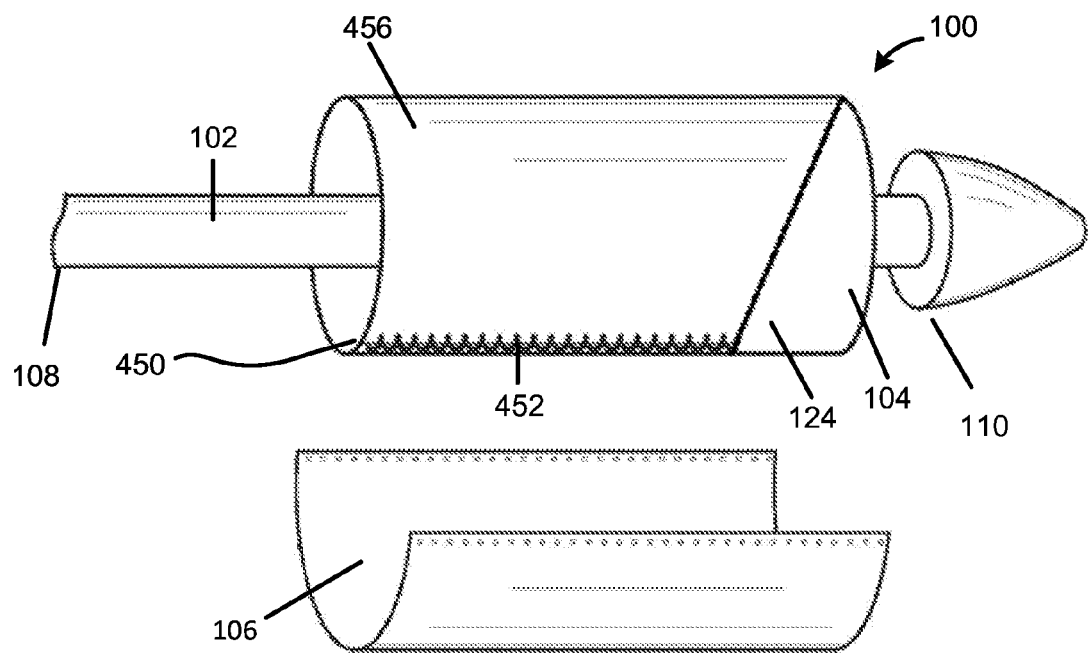

As illustrated in FIG. 4B, second sleeve 456 comprises an end profile 124. As discussed previously, end profile 124 can comprise a desired shape that exposes at least a portion of expandable implant 104.

Second sleeve 456 further comprises a second coupling member 452. Second coupling member 452 can be removed or activating, allowing expandable implant 104 to expand to an unconstrained configuration. In various embodiments, the unconstrained configuration corresponds to the desired diameter for implantation of expandable implant 104 in the treatment area of the patient.

Figure 4C:
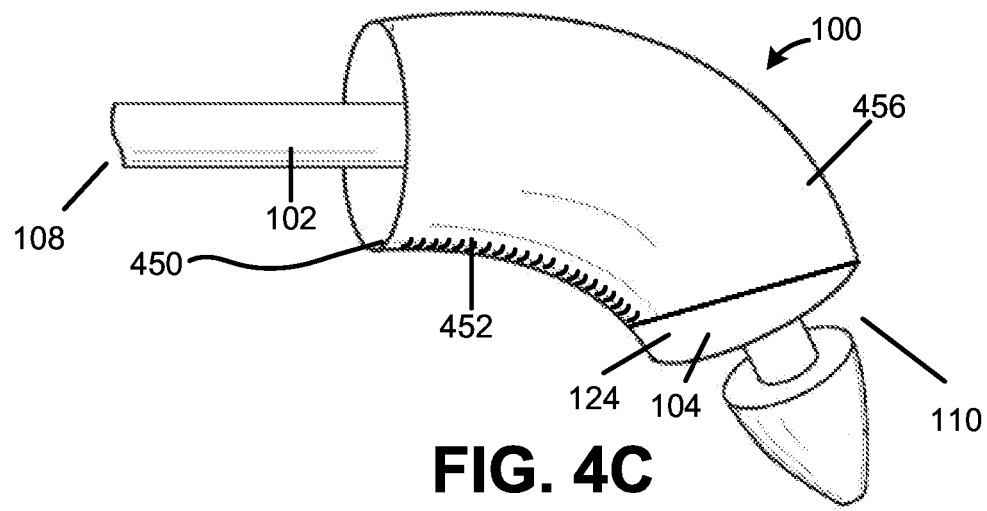
Figure 4D:
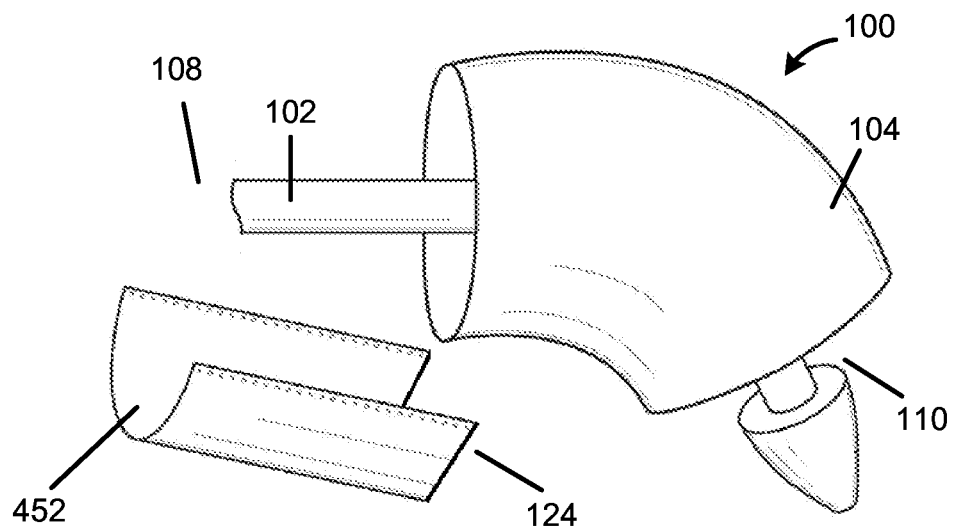

As illustrated in FIGS. 4C and 4D, catheter assembly 100 can further comprise a steering line 450. Steering line 450 can, for example, interact with second sleeve 456, and activation of steering line 450 can bend, curve, and/or conform expandable implant 104 within the vasculature of a patient. In various embodiments, steering line 450 can travel along the edge of second sleeve 456 where second coupling member 452 is located and be removably coupled to second sleeve 456 at or near the proximal end 110 of catheter 102. In such configurations, depending on the shape of end profile 124, steering line 450 can interact with the shorter edge of second sleeve 456, which can facilitate bending, curving, and/or conforming expandable implant 104 to the vasculature of the patient. However, any configuration of steering line 450 relative to expandable implant 104 and/or second sleeve 456 is within the scope of the present disclosure.

Figure 5A:
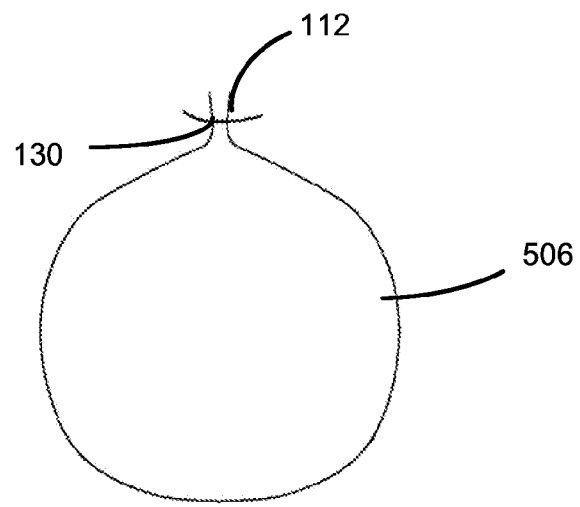
FIGS. 5A, 5B, and 5C are, respectively, two end views and a side view of an expandable medical device.
Figure 5B:
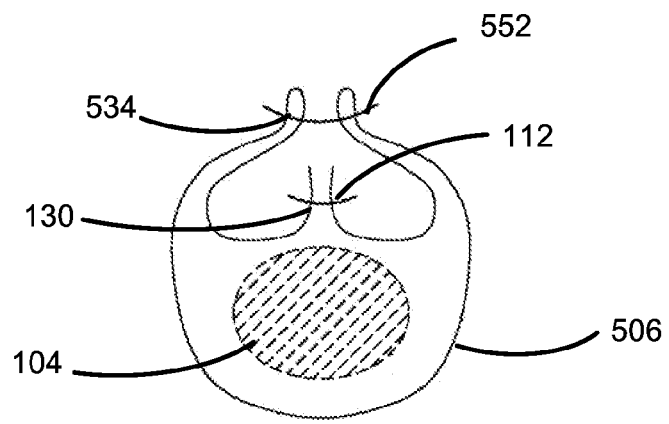

In other embodiments of the present disclosure, a single sleeve can be used to constrain the expandable implant in multiple configurations. For example, with reference to FIGS. 5A, 5B, and 5C, catheter assembly 100 comprises an expandable implant 104 and a monosleeve 506. Monosleeve 506 can be configured, for example, to maintain expandable implant 104 in both a collapsed configuration and an intermediate configuration.

In such configurations, monosleeve 506 can comprise two pluralities of holes, each corresponding to a different configuration (i.e., collapsed and intermediate) and each interacting with a different coupling member. For example, monosleeve 506 can comprise a plurality of first holes 130 and a first coupling member 112. In this configuration, first coupling member 112 is stitched or woven through the plurality of first holes 130, constricting monosleeve 506 and expandable implant 104 to the diameter of the intermediate configuration. In the intermediate configuration, the diameter of expandable implant 104 is less than the expanded diameter and larger than the diameter of the collapsed configuration. In the intermediate configuration, as described in more detail below, expandable implant 104 can be oriented and adjusted (e.g., by bending and torsional rotation) to a desired location within the treatment area of the vasculature.

Monosleeve 506 further comprises a plurality of second holes 534. In this configuration, second coupling member 552 is stitched or woven through the plurality of second holes 534, constricting monosleeve 506 and expandable implant 104 to the diameter of the collapsed configuration. The diameter of the collapsed configuration is selected to allow for delivery of the expandable implant 104 to the treatment area of the vasculature of a patient.

Once expandable implant 104 has been delivered to a region near the treatment area of the vasculature, first coupling member 112 can be disengaged from monosleeve 506, allowing expandable implant 104 to be expanded to the intermediate configuration. Expandable implant 104 can be oriented and adjusted (e.g., by bending and torsionally rotating) to a desired location within the treatment area of the vasculature. After final positioning, second coupling member 552 can be disengaged from monosleeve 506, and expandable implant 104 can be expanded to the expanded configuration.

Figure 5C:
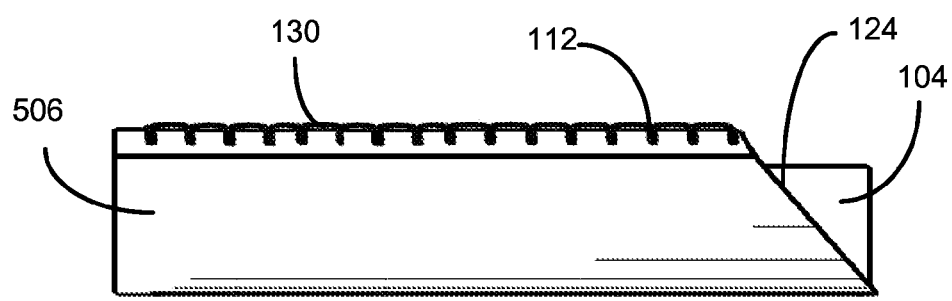

In various embodiments, as illustrated in FIG. 5C, monosleeve 506 comprises an end profile 124. For example, end profile 124 can comprise a desired shape that is consistent across the proximal end of monosleeve 506 when monosleeve 506 is in an unconstrained configuration (e.g., neither first coupling member 112 nor second coupling member 552 is engaged with monosleeve 506). However, any shape of end profile 124 relative to any configuration of monosleeve 506 (such as, for example, unconstrained, fully constrained by both first coupling member 112 and second coupling member 552, or partially constrained by first coupling member 112) is within the scope of the present disclosure.

Although a number of specific configurations of coupling members (for example, primary and secondary coupling members) and sleeves (for example primary and secondary sleeves) have been discussed, the use of any number and/or configuration of constraining members and sleeves is within the scope of the present disclosure.

It will be apparent to those skilled in the art that various modifications and variations can be made in the present disclosure without departing from the spirit or scope of the disclosure. Thus, it is intended that the present disclosure cover the modifications and variations of this disclosure provided they come within the scope of the appended claims and their equivalents.

Likewise, numerous characteristics and advantages have been set forth in the preceding description, including various alternatives together with details of the structure and function of the devices and/or methods. The disclosure is intended as illustrative only and as such is not intended to be exhaustive. It will be evident to those skilled in the art that various modifications may be made, especially in matters of structure, materials, elements, components, shape, size and arrangement of parts including combinations within the principles of the disclosure, to the full extent indicated by the broad, general meaning of the terms in which the appended claims are expressed. To the extent that these various modifications do not depart from the spirit and scope of the appended claims, they are intended to be encompassed therein.

What is claimed is:

1. A medical device comprising:
an expandable implant having a lumen comprising a central axis; and
a constraining sleeve surrounding at least a portion of the expandable implant and having a plurality of openings, the sleeve having a first end profile at a proximal end of the constraining sleeve and a second end profile at a distal end of the constraining sleeve; and
a coupling member engaging the plurality of openings and releasably closing the constraining sleeve around the portion of the expandable implant, wherein the constraining sleeve and the coupling member are configured to releaseably constrain the expandable implant in a configuration having a diameter less than a diameter of an unconstrained diameter of the expandable implant, and wherein the first end profile and the second end profile are non-perpendicular, and the second end profile of the constraining sleeve includes opposing edges tapering inwardly toward a distal end of the second end profile and exposes a portion of the expandable implant.

2. The medical device of claim 1, wherein the expandable implant is a stent-graft.

3. The medical device of claim 1, wherein the constraining sleeve maintains the expandable implant in a compressed configuration suitable for endoluminal delivery.

4. The medical device of claim 1, wherein the constraining sleeve comprises a sheet of material having first and second major surfaces and the plurality of openings extending from the first major surface to the second major surface and the coupling member cooperating with the plurality of openings for releasably coupling portions of the sheet to one another to form the constraining sleeve.

5. The medical device of claim 4, further comprising a second plurality of openings extending from the first major surface to the second major surface and a second coupling member cooperating with the second plurality of openings for releasably coupling portions of the sheet to one another to form a reduced diameter constraining sleeve, wherein the reduced diameter constraining sleeve is configured to constrain the expandable implant to a delivery configuration and wherein removal of the second coupling member causes the constraining sleeve to constrain the expandable implant to an intermediate configuration.

6. The medical device of claim 1, wherein a perimeter of the second end profile is greater than a perimeter of the first end profile.

7. The medical device of claim 1, wherein a face formed by the second end profile has an angle relative to the central axis of the expandable implant between about 30 degrees and about 60 degrees.

8. The medical device of claim 1, wherein a face formed by the second end profile has an angle relative to the central axis of the expandable implant between about 60 degrees and about 90 degrees.

9. The medical device of claim 1, wherein the constraining sleeve is expanded polytetrafluoroethylene (ePTFE).

10. A medical device comprising:
an expandable implant having a lumen comprising a central axis; and
a constraining sleeve surrounding at least a portion of the expandable implant, the sleeve having a first end profile at a proximal end of the constraining sleeve and a second end profile at a distal end of the constraining sleeve; and
a coupling member releasably closing the constraining sleeve around the portion of the expandable implant, wherein the constraining sleeve and the coupling member are configured to releaseably constrain the expandable implant in a configuration having a diameter less than a diameter of an unconstrained diameter of the expandable implant, and wherein the first end profile and the second end profile are non-perpendicular, and the second end profile of the constraining sleeve includes opposing edges tapering inwardly toward a distal end of the second end profile and exposes a portion of the expandable implant.

* * * * *